(12) United States Patent
Facciabene

(10) Patent No.: US 12,214,038 B2
(45) Date of Patent: Feb. 4, 2025

(54) COMPOSITIONS AND METHODS FOR CANCER IMMUNOTHERAPY

(71) Applicant: THE TRUSTEES OF THE UNIVERSITY OF PENNSYLVANIA, Philadelphia, PA (US)

(72) Inventor: Andrea Facciabene, Philadelphia, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 126 days.

(21) Appl. No.: 15/328,047

(22) PCT Filed: Jul. 22, 2015

(86) PCT No.: PCT/US2015/041450
§ 371 (c)(1),
(2) Date: Jun. 23, 2017

(87) PCT Pub. No.: WO2016/014613
PCT Pub. Date: Jan. 28, 2016

(65) Prior Publication Data
US 2017/0216419 A1   Aug. 3, 2017

Related U.S. Application Data

(60) Provisional application No. 62/027,691, filed on Jul. 22, 2014.

(51) Int. Cl.
*A61K 39/00* (2006.01)
*A61K 35/15* (2015.01)
*A61K 35/12* (2015.01)

(52) U.S. Cl.
CPC .......... *A61K 39/4622* (2023.05); *A61K 35/15* (2013.01); *A61K 39/4615* (2023.05); *A61K 39/464499* (2023.05); *A61K 2035/122* (2013.01)

(58) Field of Classification Search
CPC ................ A61K 39/0011; A61K 35/15; A61K 2039/5154; A61K 2035/122; A61K 2039/514; A61P 35/00
See application file for complete search history.

(56) References Cited

U.S. PATENT DOCUMENTS

| | | | |
|---|---|---|---|
| 4,708,710 A * | 11/1987 | Dunn, Jr. ............ | A61M 1/3693 210/787 |
| 5,384,253 A | 1/1995 | Krysek et al. | |
| 5,976,798 A | 11/1999 | Parker et al. | |
| 6,387,701 B1 * | 5/2002 | Nair ..................... | C12N 5/0634 435/455 |
| 2001/0033839 A1* | 10/2001 | Barbera-Guillem ........................ | A61K 39/395 424/130.1 |
| 2002/0102208 A1 | 8/2002 | Chinn et al. | |
| 2003/0096298 A1* | 5/2003 | Barnea ............. | G01N 33/56977 435/7.1 |
| 2004/0214333 A1* | 10/2004 | Liu ........................... | A61P 9/00 435/459 |
| 2006/0057129 A1* | 3/2006 | Lebkowski ......... | A61K 39/0011 424/93.21 |
| 2007/0190534 A1* | 8/2007 | Birch-Machin ...... | C12Q 1/6886 435/6.12 |
| 2007/0292448 A1 | 12/2007 | Lebkowski et al. | |
| 2008/0019998 A1 | 1/2008 | Wang et al. | |
| 2008/0241176 A1 | 10/2008 | Klinman et al. | |
| 2010/0218915 A1 | 9/2010 | Chen | |
| 2012/0189664 A1 | 7/2012 | Yu | |
| 2013/0028915 A1 | 1/2013 | Palucka et al. | |
| 2013/0210749 A1* | 8/2013 | Krissansen .............. | C07K 7/06 435/375 |
| 2014/0056845 A1 | 2/2014 | Modlin et al. | |
| 2014/0073050 A1 | 3/2014 | Nieda et al. | |
| 2014/0087468 A1 | 3/2014 | Spencer et al. | |

OTHER PUBLICATIONS

Barbosa, IA et al. Mitochondrial remodeling in cancer metabolism and survival: Potential for new therapies. Biochimica et Biophysica Acta. 2012. 1826: 238-254. (Year: 2012).*
Chaiyarit, S et al. Comparative analyses of cell disruption methods for mitochondrial isolation in high-throughput proteomics study. Analytical Biochemistry. 2009. 394: 249-258. (Year: 2009).*
Crouser, ED et al. Monocyte activation by necrotic cells is promoted by mitochondrial proteins and formyl peptide receptors. Crit. Care Med. 2009. 37(6): 2000-2009. (Year: 2009).*
Chatterjee, A et al. Mitochondrial DNA mutations in human cancer. Oncogene. 2006. 25: 4663-4674. (Year: 2006).*
Voo et al. CD4+T-Cell Response to Mitochondrial Cytochrome b in Human Melanorma, Jun. 1, 2006, Cancer Research, vol. 66, No. 11, p. 5919-5926.
Jakupciak et al. "Performance of mitochondrial DNA mutations detecting early stage cancer" BMC Cancer, Oct. 3, 2008, vol. 8, No. 285, pp. 1-11.
Nishikawa et al. "Somatic Mutation of Mitochondrial DNA in Cancerous and Noncancerous Liver Tissue in Individuals with Hepatocellular Carcinoma," Cancer Research, Mar. 1, 2001, vol. 61, p. 1843-1845.
Morris et al. "Phase I Trial of BCL-2 Antisense Oligonucleotide (G3139) Administered by Continuous Intravenous Infusion in Patients with Advanced Cancer," Clinical Cancer Research, Mar. 1, 2002.
Sakinah et al. "Zerumbone induced apoptosis in liver cancer cells via modulation of BAX/BCI-2 ratio," Cancer Cell International, Apr. 3, 2007, vol. 7, No. 4, pp. 1-11.

(Continued)

*Primary Examiner* — David W Berke-Schlessel
*Assistant Examiner* — Susan E. Fernandez
(74) *Attorney, Agent, or Firm* — Mark S. Cohen; PEARL COHEN ZEDEK LATZER BARATZ LLP

(57) ABSTRACT

The invention provides compositions and methods for cancer immunotherapy. Specifically, the invention provides an antigen-presenting cell, for example, a dendritic cell that comprises a tumor mitochondrial molecule or a tumor mitochondrial molecule derived from tumor mitochondrial protein lysate or a specific mitochondria derived protein of mitochondrial protein lysate as antigen source.

14 Claims, 5 Drawing Sheets
Specification includes a Sequence Listing.

(56) References Cited

OTHER PUBLICATIONS

Gasparre et al. "Clonal expansion of mutated mitochondrial DNA is associated with tumor formation and complex I defiency in the benign renal oncocytoma," Human Molecular Genetics, Dec. 21, 2007, vol. 17, No. 7, pp. 986-995.

Khaidakov et al. "Contribution of de novo point mutations to the overall mutational burden in mitochondrial DNA of adult rats," Experimental Gerontology, Mar. 28, 2005, vol. 40, pp. 396-402, entire document.

Dasgupta et al. Mitochondrial DNA Mutations in Respiratory Complex-I in Never-Smoker Lung Cancer Patients Contribute to Lung Cancer Progression and associated with EGFR gene 2451-2460 (pp. 1-21 for citations). entire document.

Acin-Perez et al. An intragenic suppressor in the cytochrome c oxidase I gene of mouse mitochondrial DNA. Human Molecular Genetics, vol. 12, No. 3, pp. 329-339, Feb. 1, 2003.

Yin et al. "Somatic mutations of mitochondrial genome in hepatocellular carcinoma," Mitochondrian, Dec. 16, 2009, vol. 10, Pgs.

Gefter et al., "A simple method for polyethylene glycol-promoted hybridization of mouse myeloma cells." Somatic cell genetics 3.2 (1977): 231-236.

International Preliminary Report on Patentability from PCT/US2015/041450 dated Feb. 2, 2017.

Morstyn, George, and William Sheridan, eds. Cell therapy: stem cell transplantation, gene therapy, and cellular immunotherapy. Cambridge University Press, 1996, pp. 922-926.

Potter, et al., "Enhancer-dependent expression of human kappa immunoglobulin genes introduced into mouse pre-B lymphocytes by electroporation." Proceedings of the National Academy of Sciences 81.22 (1984): 7161-7165.

Steinman, Ralph M. "The dendritic cell system and its role in immunogenicity." Annual review of immunology 9.1 (1991): 271-296.

Tur-Kaspa, R., et al. "Use of electroporation to introduce biologically active foreign genes into primary rat hepatocytes." Molecular and cellular biology 6.2 (1986): 716-718.

\* cited by examiner

ADOPTIVE SCHEDULE

MEMORY SCHEDULE

COMPOSITIONS AND METHODS FOR CANCER IMMUNOTHERAPY

This application is a National Phase Application of PCT International Application No. PCT/US15/041450, International Filing Date Jul. 22, 2015, claiming priority of U.S. Provisional Patent Applications No. 62/027,691, filed Jul. 22, 2014, which is/are hereby incorporated by reference.

FIELD OF THE INVENTION

The invention relates generally to compositions and methods for cancer immunotherapy. Specifically, the invention relates to an antigen-presenting cell, for example, a dendritic cell that comprises a tumor mitochondrial molecule derived from tumor mitochondrial protein lysate or a specific mitochondria derived protein of mitochondrial protein lysate as an antigen source.

BACKGROUND OF THE INVENTION

Cancer immunotherapy is based on the recognition and targeting of cancer specific antigens by immune cells. Dendritic cell vaccines for eliciting an immune response against certain tumor targets are known in the art.

Dendritic cells (DCs) are antigen-presenting cells of the mammalian immune system. They process antigen material and present it on the cell surface to the T cells of the immune system in a major histocompatibility complex (MHC)-restricted fashion. These cells act as messengers between the innate and the adaptive immune systems.

DCs are present in tissues that are in contact with the external environment, for example, the skin and the inner lining of the nose, lungs, stomach and intestines. They can also be found in an immature state in the blood. Once activated, the cells migrate to the lymph nodes where they interact with T cells and B cells to initiate and shape the adaptive immune response.

The discovery of the role of DCs as antigen-presenting cells (APCs) has fueled attempts at DC-based immunization/vaccination for cancer therapy that involve loading DCs with tumor specific antigens through transfection with vectors expressing the specific antigen, tumor lysate, peptides, or full proteins. However, to date, not much work has been done with respect to mitochondria as source of antigen for cancer immunotherapy.

Accordingly, there exists a need for understanding the role of mitochondria as an antigen source to develop vaccines and compositions for cancer immunotherapy.

SUMMARY OF THE INVENTION

In one aspect, the invention provides an immunogenic composition comprising: an antigen-presenting cell (e.g., dendritic cell) that comprises a tumor antigen, wherein said tumor antigen is a tumor mitochondrial molecule derived from a tumor mitochondrial protein lysate or a specific mitochondria derived protein of mitochondrial protein lysate.

In another aspect, the invention provides a method for stimulating an anti-tumor immune response in a subject, the method comprising: administering a therapeutically effective amount of an immunogenic composition to said subject, said immunogenic composition comprising an antigen-presenting cell (e.g., dendritic cell) that comprises a tumor antigen, wherein said tumor antigen is a tumor mitochondrial molecule derived from tumor mitochondrial protein lysate or a specific mitochondria derived protein of mitochondrial protein lysate.

In another aspect, the invention provides a method for treating a renal cancer by immunotherapy in a subject, the method comprising: administering a therapeutically effective amount of an immunogenic composition to said subject, said immunogenic composition comprising an antigen-presenting cell (e.g., dendritic cell) that comprises a tumor antigen, wherein said tumor antigen is a tumor mitochondrial molecule derived from tumor mitochondrial protein lysate or a specific mitochondria derived protein of mitochondrial protein lysate.

In another aspect, the invention provides a method for treating a liver cancer by immunotherapy in a subject, the method comprising: administering a therapeutically effective amount of an immunogenic composition to said subject, said immunogenic composition comprising an antigen-presenting cell (e.g., dendritic cell) that comprises a tumor antigen, wherein said tumor antigen is a tumor mitochondrial molecule derived from tumor mitochondrial protein lysate or a specific mitochondria derived protein of mitochondrial protein lysate.

In another aspect, the invention provides an immunogenic composition comprising: an antigen-presenting cell that comprises a tumor mitochondrial antigen, wherein said tumor mitochondrial antigen is a tumor mitochondrial Cyclooxygenase-1 (COX-1), Cyclooxygenase-2 (COX-2), NADH dehydrogenase 5 (ND5), or NADH dehydrogenase 6 (ND6) molecule.

In another aspect, the invention provides a method for stimulating an anti-tumor immune response in a subject, the method comprising: administering a therapeutically effective amount of an immunogenic composition to said subject, said immunogenic composition comprising an antigen-presenting cell that comprises a tumor mitochondrial antigen, wherein said tumor mitochondrial antigen is a tumor mitochondrial Cyclooxygenase-1 (COX-1), Cyclooxygenase-2 (COX-2), NADH dehydrogenase 5 (ND5), or NADH dehydrogenase 6 (ND6) molecule.

In another aspect, the invention provides a method for treating a cancer (e.g., renal cancer or liver cancer) by immunotherapy in a subject, the method comprising: administering a therapeutically effective amount of an immunogenic composition to said subject, said immunogenic composition comprising an antigen-presenting cell that comprises a tumor mitochondrial antigen, wherein said tumor mitochondrial antigen is a tumor mitochondrial Cyclooxygenase-1 (COX-1), Cyclooxygenase-2 (COX-2), NADH dehydrogenase 5 (ND5), or NADH dehydrogenase 6 (ND6) molecule.

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

DETAILED DESCRIPTION OF THE INVENTION

Figure 1A:
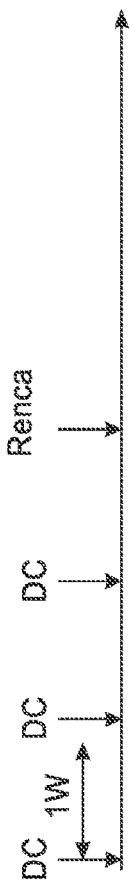
FIG. 1 shows that tumor mitochondria protein pulsed dendritic cell immunization confers tumor protection. A. prophylactic schedule. B. Reduction in tumor volume—Administration of these tumor mitochondria-pulsed BM-DC resulted in rejection of 70 percent of tumors when the vaccine was given prophylactically and 50 percent of tumors when given therapeutically. C. Spoot per $1\times10^6$ splenocytes—100.000 purified CD3+ T cells isolated from splenocytes of vaccinated animals were exposed to tumor cells at a ratio of 10:1 in interferon gamma ELISPOT assay.

The invention relates generally to compositions and methods for cancer immunotherapy. Specifically, the invention relates to an antigen-presenting cell, for example, a dendritic cell that comprises a tumor mitochondrial molecule derived from tumor mitochondrial protein lysate or a specific mitochondria derived protein of mitochondrial protein lysate as antigen source.

The inventors of the instant application surprisingly and unexpectedly found that pulsing dendritic cells with mitochondria protein lysate from renal or hepato-carcinoma, followed by lipopolysaccharide (LPS) and interferon-gamma (IFNg) treatment led to the production of dendritic cell vaccines with robust anti-tumor activities. In mouse models, the administration of dendritic cell vaccines surprisingly and unexpectedly induced specific T cell anti-tumor responses. Activated T cells recognized specific tumor antigens and directly killed tumor cells.

In one aspect, provided herein is a composition comprising: an antigen-presenting cell (e.g., dendritic cell) that comprises a tumor antigen, wherein said tumor antigen is a tumor mitochondrial molecule derived from tumor mitochondrial protein lysate or a specific mitochondria derived protein of mitochondrial protein lysate.

The term "antigen," as used herein, refers to a molecule that provokes an immune response. This immune response may involve either antibody production, or the activation of specific immunologically-competent cells, or both. An antigen can be derived from organisms, subunits of proteins/antigens, killed or inactivated whole cells or lysates. Therefore, a skilled artisan realizes that any macromolecule, including virtually all proteins or peptides, can serve as antigens. Furthermore, antigens can be derived from mitochondria. In an exemplary embodiment, the antigen of the invention is a mitochondrial protein lysate. It is readily apparent that the present invention includes, but is not limited to, the use of a molecule, a group of molecules, a substance, or a mitochondria organelle, capable of eliciting a desired immune response.

In an exemplary embodiment, the antigen of the invention is a mitochondrial protein lysate. Methods or techniques for obtaining a mitochondrial protein lysate are well known in the art. Tumor cells or tissues can be obtained and mitochondrial proteins can be pelleted using a lysis buffer, using any suitable method or technique known to one of skilled in the art, in order to obtain a mitochondrial protein lysate. In another exemplary embodiment, the antigen of the invention is a tumor mitochondrial mutant molecule, for example, a tumor mitochondrial Cyclooxygenase-1 (COX-1), Cyclooxygenase-2 (COX-2), NADH dehydrogenase 5 (ND5), or NADH dehydrogenase 6 (ND6) molecule0A. Methods for preparing these molecules are well known in the art. In some embodiments, the COX-1 molecule comprises a G6234A mutation. In some embodiments, the COX-2 molecule comprises a G7292A. In some embodiments, the ND5 molecule comprises a C13330A mutation. In some embodiments, the ND6 molecule comprises a T13884T>C mutation.

The term "pulse" or "pulsing," as used herein may refer to causing an antigen-presenting cell to react, directly or indirectly, with a substance, for example, mitochondrial molecule or protein lysate.

The term "antigen-presenting cell" is any of a variety of cells capable of acquiring, processing, presenting, or displaying at least one antigen or antigenic fragment on (or at) its cell surface. In general, the term "antigen-presenting cell" can be any cell that accomplishes the goal of the invention by aiding the enhancement of an immune response (i.e., from the T-cell or -B-cell arms of the immune system) against an antigen or antigenic composition. Such cells can be defined by those of skill in the art, using methods disclosed herein and in the art. As is understood by one of ordinary skill in the art (See for example Kuby, 2000, *Immunology*, 4th edition, W. H. Freeman and company, incorporated herein by reference), and used herein in certain embodiments, a cell that displays or presents an antigen normally or preferentially with a class II major histocompatibility molecule or complex to an immune cell is an "antigen-presenting cell." In certain aspects, a cell (e.g., an antigen-presenting cell) may be fused with another cell, such as a recombinant cell or a tumor cell that expresses the desired antigen. Methods for preparing a fusion of two or more cells is well known in the art, such as for example, the methods disclosed in Goding, J. W., Monoclonal Antibodies: Principles and Practice, pp. 65-66, 71-74 (Academic Press, 1986); Campbell, in: Monoclonal Antibody Technology, Laboratory Techniques in Biochemistry and Molecular Biology, Vol. 13, Burden & Von Knippenberg, Amsterdam, Elseview, pp. 75-83, 1984; Kohler & Milstein, *Nature*, 256:495-497, 1975; Kohler & Milstein, *Eur. J. Immunol.*, 6:511-519, 1976, Gefter et al., *Somatic Cell Genet.*, 3:231-236, 1977, each incorporated herein by reference. In some cases, the immune cell to which an antigen-presenting cell displays or presents an antigen to is a CD4+ TH cell. Additional molecules expressed on the antigen-presenting cells or other immune cells may aid or improve the enhancement of an immune response. Secreted or soluble molecules, such as for example, cytokines and adjuvants, may also aid or enhance the immune response against an antigen. Such molecules are well known to one of skill in the art, and various examples are described herein.

In an exemplary embodiment, antigen-presenting cell is a dendritic cell. Other antigen-presenting cells are also within the scope of the invention.

As used herein, dendritic cell (DC) may refer to any member of a diverse population of morphologically similar cell types found in lymphoid or non-lymphoid tissues. DCs may include, for example, "professional" antigen presenting cells, and have a high capacity for sensitizing MHC-restricted T cells. DCs may be recognized, for example, by function, by phenotype and/or by gene expression pattern, particularly by cell surface phenotype. These cells can be characterized by their distinctive morphology, high levels of surface MHC-class II expression and ability to present antigen to CD4+ and/or CD8+ T cells, particularly to naive T cells (Steinman et al. (1991) *Ann. Rev. Immunol.* 9:271; incorporated herein by reference for its description of such cells).

Functionally, DCs may be identified by any suitable assay, known to one of skilled in the art, for determination of antigen presentation. Such assays may include, for example, testing the ability to stimulate antigen-primed and/or naive T cells by presentation of a test antigen, followed by determination of T cell proliferation, release of IL-2, and the like.

In some embodiments, DCs are autologous (i.e., derived from the subject to be treated). In other embodiments, DCs are obtained from a donor (i.e., allogeneic), for example, from a compatible donor, i.e., HLA typed so that they are histocompatible with the subject into which they will be transplanted.

DCs can be generated by the methods well known in the art. These methods are described in U.S. Patent Applications U.S. 2007/0292448; U.S. 2008/0241176; U.S. 2008/0019998; U.S. 2010/0218915; U.S. 2014/0073050; U.S. 2014/0087468; U.S. 2014/0056845; and U.S. 2013/0028915, which are incorporated by reference herein in their entirety.

For instance, for the preparation of the dendritic cells, a sample can be acquired for obtaining precursors of the dendritic cells. Examples of this sample, include, but are not limited to, a peripheral blood sample, bone marrow sample, umbilical cord blood or the like. Any suitable method, known to one of skilled in the art, can be used for collecting samples. In one embodiment, the method for collecting the blood is a whole blood collection using, for example, a vacuum blood collection tube or a blood collection bag. Also, when a large amount of cells is needed, peripheral blood mononuclear cells can be directly obtained by employing a method of collecting a mononuclear cell fraction using an apheresis instrument. For avoiding coagulation, heparin or a citric acid may be added to the collected blood.

Mononuclear cells may include the precursors of the dendritic cells. Such mononuclear cells containing the precursors of the dendritic cells can be separated from the collected blood, by a known method. For example, the separation can be carried out by any method of separating nuclear cells from erythrocytes. In one embodiment, a method utilizing Ficoll fractionation, i.e., Ficoll-Paque density gradient or elution is employed generally. In a preferred embodiment, the collected cells are washed several times using a culture medium, a physiological saline solution, or a phosphate buffered saline for the purpose of removing thrombocytes.

After the collected mononuclear cells, monocytes, which are the CD14-positive cells and precursors of the dendritic cells, are separated from the collected mononuclear cells. CD14 is known as a marker that is expressed in monocytes. In preferred embodiment, the monocytes can be isolated and collected with Magnetic Cell Sorting using anti-CD14 antibody magnetic beads. Alternate methods, known in the art, can also be used for the recovery of monocytes.

The next step may include, for example, differentiation induction of immature dendritic cells or mature dendritic cells from the obtained precursors of the dendritic cells. Any suitable induction medium known to one of skilled in the art can be used. Examples of such medium, include, but not limited to, an AIM-V medium (Invitrogen Corporation), an RPMI-1640 medium (Invitrogen Corporation), Dulbecco's Modified Eagle Medium (Invitrogen Corporation), TIL (Immuno-Biological Laboratories Co., Ltd.), an epidermal keratinocyte medium (Kohjin Bio Co., Ltd.) and Iscove's medium (Invitrogen Corporation). In some embodiments, bovine serum, fetal bovine serum, human serum, human plasma, or combination thereof, can be added to the medium.

For obtaining the immature dendritic cells, a differentiation inducer can be added to the culture medium so as to culture the precursors of the dendritic cells. For obtaining the mature dendritic cells, a further differentiation inducer is added on day 5 to day 7 after starting culture, followed by further culturing. In one embodiment, the differentiation inducer is a cytokine, for example, a granulocyte macrophage colony stimulating factor (GM-CSF), interleukin (IL) 4, a stem cell factor (SCF), IL-1, IL-2, or IL-3, IL-13, a tumor necrosis factor alpha (TNF-alpha), prostaglandin E2, or a combination thereof. The culture can be incubated at a temperature ranging from about at 34° C. to 38° C., preferably 37° C., under a condition of approximately 2% to 10% $CO_2$, preferably 5% $CO_2$, and the culture period preferably is 1 to 7 days.

In some embodiments, one of skill in the art can use a method including collecting hematopoietic stem cells (CD34-positive cells) as the precursors of the dendritic cells and adding thereto GM-CSF, TNF-alpha and flt-3 ligand (FL), c-kit ligand (SCF) or thrombopoietin (TPO) solely or in combination, thus obtaining the immature dendritic cells or the mature dendritic cells. In other embodiments, one of skilled in the art can use a method including collecting dendritic cell fractionation directly from blood or separated peripheral blood mononuclear cells using a density gradient solution such as Percoll.

The resultant antigen-presenting cells (e.g., the immature dendritic cells or the mature dendritic cells) can be frozen in liquid nitrogen (or equivalent) prior to use. If frozen, the cells may be stored in a medium, for example, 10% DMSO, 50% FCS, 40% RPMI 1640 medium in liquid nitrogen, or other suitable medium known in the art.

Dendritic cells of the invention may have functional activities and phenotypes that are specifically associated with the maturity of the cell. Cell surface markers useful in the characterization of and classification of dendritic cells include, for example, but not limited to: CD1, CD11a; CD11b; CD11c; F4/80; Fc gamma RII/III receptor (FcR); MHC class I; MHC class II; CD80; CD86; CD54; CD40; and CD117.

The cell surface can be analyzed, for example, using suitable marker-specific monoclonal antibodies (e.g., sorting by flow cytometry, magnetic sorting, immunobead selection, immunopanning, etc.). In some embodiments, the phenotypic characteristics of dendritic cells can be characterized by gene expression profiling e.g. by reverse-transcriptase polymerase chain reaction (RT-PCR).

In some embodiments, the antigen-presenting cells (e.g., DCs) of the present invention are activated by a method known to one of skilled in the art.

The antigen-presenting cells (e.g., DCs) of the invention can be pulsed with an antigen (e.g., tumor mitochondrial molecule derived from tumor mitochondrial protein lysate, a specific mitochondria derived protein of mitochondrial protein lysate, or mitochondrial protein lysate) by a method known to one of skilled in the art. In one example, the antigen is transfected or introduced into the antigen-presenting cells by a method known to one of skilled in the art.

Appropriate physical and/or chemical conditions can be provided for pulsing or transfections.

Examples of transfecting or introducing antigen into the antigen-presenting cells include, for example, but are not limited to, electroporation, injection, sonication loading, liposome-mediated transfection, and receptor-mediated transfection.

In a particular embodiment, the introduction of antigen into the antigen-presenting cells is performed by electroporation. Electroporation may involve the exposure of a suspension of cells and antigen to a high-voltage electric discharge. In some variants of this method, certain cell wall-degrading enzymes, such as pectin-degrading enzymes, are employed to render the target recipient cells more susceptible to transformation by electroporation than untreated cells. Electroporation methods are well known in the art. (See e.g., U.S. Pat. No. 5,384,253; Potter et al., 1984, *Proc. Nat'l Acad. Sci. USA*, vol. 81, pages 7161-7165; Tur-Kaspa et al., 1986, *Mol. Cell. Biol.,* 6, 716-718, all of which are incorporated by reference herein in their entirety).

The modified antigen-presenting cells (e.g., DCs) can be transferred to a recipient in any physiologically acceptable excipient comprising an isotonic excipient prepared under sufficiently sterile conditions for human administration. Cell based therapy and medicinal formulations are well known in the art. See e.g., Cell Therapy: Stem Cell Transplantation, Gene Therapy, and Cellular Immunotherapy, by G. Morstyn & W. Sheridan eds, Cambridge University Press, 1996, which is incorporated by reference herein.

In another aspect, the invention provides a pharmaceutical composition comprising a therapeutically effective amount of an antigen-presenting cell (e.g., dendritic cell) that comprises a tumor antigen, for example, a tumor mitochondrial molecule or a tumor mitochondrial protein lysate.

In a particular embodiment, the pharmaceutical composition is in the form of a vaccine. As used herein, the term "vaccine" may refer to a formulation which contains a composition presented herein which is in a form that is capable of being administered to a human or an animal. In one example, the vaccine comprises a conventional saline or buffered aqueous solution medium in which the composition is suspended or dissolved. In this form, the composition can be used conveniently to prevent, ameliorate, or otherwise treat a condition. Upon introduction into a subject, the vaccine is able to provoke an immune response including, but not limited to, the production of antibodies, cytokines and/or other cellular responses. In some embodiments, an expression construct, expression vector and/or transduced antigen-presenting cells can enhance or contribute to the effectiveness of a vaccine by, for example, enhancing the immunogenicity of weaker antigens such as highly purified or recombinant antigens, reducing the amount of antigen required for an immune response, reducing the frequency of immunization required to provide protective immunity, improving the efficacy of vaccines in subjects with reduced or weakened immune responses, such as newborns, the aged, and immunocompromised individuals, and enhancing the immunity at a target tissue, such as mucosal immunity, or promote cell-mediated or humoral immunity.

In one example, an immunocompromised individual or subject is a subject that has a reduced or weakened immune response. Such individuals may also include a subject that has undergone chemotherapy or any other therapy resulting in a weakened immune system, a transplant recipient, a subject currently taking immunosuppressants, an aging individual, or any individual that has a reduced and/or impaired CD4 T helper cells. It is contemplated that the present methods can be utilized to enhance the amount and/or activity of CD4 T helper cells in an immunocompromised subject.

The pharmaceutical composition of the invention may include appropriate pharmaceutically acceptable carriers, known to one of skilled in the art. "Pharmaceutically acceptable carriers" include any excipient which is nontoxic to the cell or mammal being exposed thereto at the dosages and concentrations employed. The pharmaceutical composition may include one or additional therapeutic agents.

Pharmaceutically acceptable carriers include solvents, dispersion media, buffers, coatings, antibacterial and antifungal agents, wetting agents, preservatives, buggers, chelating agents, antioxidants, isotonic agents and absorption delaying agents.

Pharmaceutically acceptable carriers include water; saline; phosphate buffered saline; dextrose; glycerol; alcohols such as ethanol and isopropanol; phosphate, citrate and other organic acids; ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; EDTA; salt forming counterions such as sodium; and/or nonionic surfactants such as TWEEN, polyethylene glycol (PEG), and PLURONICS; isotonic agents such as sugars, polyalcohols such as mannitol and sorbitol, and sodium chloride; as well as combinations thereof. Antibacterial and antifungal agents include parabens, chlorobutanol, phenol, ascorbic acid, and thimerosal.

The pharmaceutical compositions of the invention may be formulated in a variety of ways, including for example, liquid, semi-solid and solid dosage forms, such as liquid solutions (e.g., injectable and infusible solutions), dispersions or suspensions, tablets, pills, powders, liposomes and suppositories. In some embodiments, the compositions are in the form of injectable or infusible solutions. The composition is in a form suitable for oral, intravenous, intraarterial, intramuscular, subcutaneous, parenteral, transmucosal, transdermal, or topical administration. The composition may be formulated as an immediate, controlled, extended or delayed release composition.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. In the subject invention, pharmaceutically acceptable carriers include, but are not limited to, 0.01-0.1M and preferably 0.05M phosphate buffer or 0.8% saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present such as for example, antimicrobials, antioxidants, chelating agents, and inert gases and the like.

More particularly, pharmaceutical compositions suitable for injectable use include sterile aqueous solutions (where water soluble) or dispersions and sterile powders for the extemporaneous preparation of sterile injectable solutions or dispersions. In such cases, the composition must be sterile and should be fluid to the extent that easy syringability exists. It should be stable under the conditions of manufacture and storage and will preferably be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Suitable formulations for use in the therapeutic methods disclosed herein are described in Remington's Pharmaceutical Sciences, Mack Publishing Co., 16$^{th}$ ed. (1980).

In some embodiments, the composition includes isotonic agents, for example, sugars, polyalcohols, such as mannitol, sorbitol, or sodium chloride. Prolonged absorption of the injectable compositions can be brought about by including in the composition an agent which delays absorption, for example, aluminum monostearate and gelatin.

Sterile injectable solutions can be prepared by incorporating the molecule, by itself or in combination with other active agents, in the required amount in an appropriate solvent with one or a combination of ingredients enumerated herein, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, one method of preparation is vacuum drying and freeze-drying, which yields a powder of an active ingredient plus any additional desired ingredient from a previously sterile-filtered solution thereof. The preparations for injections are processed, filled into containers such as ampoules, bags, bottles, syringes or vials, and sealed under aseptic conditions according to methods known in the art. Further, the preparations may be packaged and sold in the form of a kit such as those described in US Appl. Publ. No. 2002/0102208 A1, which is incorporated herein by reference in its entirety. Such articles of manufacture will preferably have labels or package inserts indicating that the associated compositions are useful for treating a subject suffering from, or predisposed to autoimmune or neoplastic disorders.

Effective doses of the compositions of the present invention, for treatment of conditions or diseases as described herein vary depending upon many different factors, including means of administration, target site, physiological state of the patient, whether the patient is human or an animal, other medications administered, and whether treatment is prophylactic or therapeutic. Usually, the patient is a human but non-human mammals including transgenic mammals can also be treated. Treatment dosages may be titrated using routine methods known to those of skill in the art to optimize safety and efficacy.

The pharmaceutical compositions of the invention may include a "therapeutically effective amount." A "therapeutically effective amount" refers to an amount effective, at dosages and for periods of time necessary, to achieve the desired therapeutic result. A therapeutically effective amount of a molecule may vary according to factors such as the disease state, age, sex, and weight of the individual, and the ability of the molecule to elicit a desired response in the individual. A therapeutically effective amount is also one in which any toxic or detrimental effects of the molecule are outweighed by the therapeutically beneficial effects.

The invention further provides a kit comprising a therapeutically effective amount of an antigen-presenting cell (e.g., a dendritic cell) that comprises a tumor antigen, wherein said tumor antigen is a tumor mitochondrial protein lysate.

The invention further provides methods of treating a disease or condition, comprising administering to a mammal in need thereof a therapeutically effective amount of a composition comprising a dendritic cell that comprises a tumor mitochondrial antigen of the invention. In one aspect, the invention provides a method for stimulating an anti-tumor immune response in a subject, the method comprising: administering a therapeutically effective amount of an immunogenic composition to said subject, said immunogenic composition comprising a dendritic cell that comprises a tumor mitochondrial antigen of the invention. In another aspect the invention provides a method for treating a cancer by immunotherapy in a subject, the method comprising: administering a therapeutically effective amount of an immunogenic composition to said subject, said immunogenic composition comprising a dendritic cell that comprises a tumor mitochondrial antigen of the invention.

As used herein, the terms "treat" and "treatment" refer to therapeutic treatment, including prophylactic or preventative measures, wherein the object is to prevent or slow down (lessen) an undesired physiological change associated with a disease or condition. Beneficial or desired clinical results include, but are not limited to, alleviation of symptoms, diminishment of the extent of a disease or condition, stabilization of a disease or condition (i.e., where the disease or condition does not worsen), delay or slowing of the progression of a disease or condition, amelioration or palliation of the disease or condition, and remission (whether partial or total) of the disease or condition, whether detectable or undetectable. "Treatment" can also mean prolonging survival as compared to expected survival if not receiving treatment. Those in need of treatment include those already with the disease or condition as well as those prone to having the disease or condition or those in which the disease or condition is to be prevented.

Cancers/tumors which may be treated by the invention include any cancer or tumor. Examples of cancers/tumors which may be treated include, but are not limited to, renal cancer, kidney cancer, liver cancer, and breast cancer.

Methods of treating cancer include, but are not limited to, e.g., inhibiting angiogenesis in the tumor, inhibiting tumor growth, inhibiting tumor migration, inhibiting proliferation or inhibiting invasion of tumor cells.

Cancers to be treated include primary tumors and secondary or metastatic tumors (including those metastasized from lung, breast, or prostate), as well as recurrent or refractory tumors. Recurrent tumors encompass tumors that appear to be inhibited by treatment with such agents, but recur up to five years, sometimes up to ten years or longer after treatment is discontinued. Refractory tumors are tumors that have failed to respond or are resistant to treatment with one or more conventional therapies for the particular tumor type. Refractory tumors include those that are hormone-refractory; those that are refractory to treatment with one or more chemotherapeutic agents; those that are refractory to radiation; and those that are refractory to combinations of chemotherapy and radiation, chemotherapy and hormone therapy, or hormone therapy and radiation Therapy may be "first-line", i.e., as an initial treatment in patients who have had no prior anti-cancer treatments, either alone or in combination with other treatments; or "second-line", as a treatment in patients who have had one prior anti-cancer treatment regimen, either alone or in combination with other treatments; or as "third-line", "fourth-line", etc. treatments, either alone or in combination with other treatments.

Therapy may also be given to patients who have had previous treatments which have been partially successful but are intolerant to the particular treatment. Therapy may also be given as an adjuvant treatment, i.e., to prevent reoccurrence of cancer in patients with no currently detectable disease or after surgical removal of tumor.

Cancers that may be treated include tumors that are not vascularized, or not yet substantially vascularized, as well as vascularized tumors. The cancers may be comprised of non-solid tumors (such as leukemias and lymphomas) or may be solid tumors. Types of cancers to be treated with the antibodies of the invention include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are included.

The composition of the invention may be administered alone, or in combination with one or more therapeutically effective agents or treatments. The other therapeutically effective agent may be conjugated to the components of the antigen-presenting cells, incorporated into the same composition as the antigen-presenting cells, or may be administered as a separate composition. The other therapeutically agent or treatment may be administered prior to, during and/or after the administration of the composition of the invention.

In one embodiment, the composition of the invention is co-administered with one or more other therapeutic agents. In another embodiment, the composition of the invention is administered independently from the administration of one or more other therapeutic agents. In one embodiment, the composition of the invention is administered first, followed by the administration of one or more other therapeutic agents. In another embodiment, one or more other therapeutic agents are administered first, followed by the administration of the composition of the invention.

Other therapeutically effective agents/treatments include surgery, anti-neoplastics (including chemotherapeutic agents and radiation), anti-angiogenesis agents, antibodies to other targets, small molecules, photodynamic therapy, immunotherapy, cytotoxic agents, cytokines, chemokines, growth inhibitory agents, anti-hormonal agents, kinase inhibitors, cardioprotectants, immunostimulatory agents, immunosuppressive agents, agents that promote proliferation of hematological cells, and protein tyrosine kinase (PTK) inhibitors.

The administration of the composition of the invention with other agents and/or treatments may occur simultaneously, or separately, via the same or different route, at the same or different times. Dosage regimens may be adjusted to provide the optimum desired response (e.g., a therapeutic or prophylactic response).

In one example, a single bolus may be administered. In another example, several divided doses may be administered over time. In yet another example, a dose may be proportionally reduced or increased as indicated by the exigencies of the therapeutic situation. Dosage unit form, as used herein, refers to physically discrete units suited as unitary dosages for treating mammalian subjects. Each unit may contain a predetermined quantity of active compound calculated to produce a desired therapeutic effect. In some embodiments, the dosage unit forms of the invention are dictated by and directly dependent on the unique characteristics of the active compound and the particular therapeutic or prophylactic effect to be achieved.

The composition of the invention may be administered only once, or it may be administered multiple times. For multiple dosages, the composition may be, for example, administered three times a day, twice a day, once a day, once every two days, twice a week, weekly, once every two weeks, or monthly.

It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

"Administration" to a subject is not limited to any particular delivery system and may include, without limitation, parenteral (including subcutaneous, intravenous, intramedullary, intraarticular, intramuscular, or intraperitoneal injection) rectal, topical, transdermal or oral (for example, in capsules, suspensions or tablets). Administration to a host may occur in a single dose or in repeat administrations, and in any of a variety of physiologically acceptable salt forms, and/or with an acceptable pharmaceutical carrier and/or additive as part of a pharmaceutical composition (described earlier). Once again, physiologically acceptable salt forms and standard pharmaceutical formulation techniques are well known to persons skilled in the art (see, for example, Remington's Pharmaceutical Sciences, Mack Publishing Co.).

The composition of the invention may be administered parenterally (e.g., intravenous, subcutaneous, intraperitoneal, intramuscular). Further, the composition of the invention may be administered by intravenous infusion or injection. The composition of the invention may be administered by intramuscular or subcutaneous injection. In some embodiments, the composition of the invention may be administered orally. As used herein, a "composition" refers to any composition that contains a pharmaceutically effective amount of an antigen-presenting cell (e.g., a dendritic cell) that comprises a tumor antigen, wherein said tumor antigen is a tumor mitochondrial protein lysate.

The methods of treatment described herein can be used to treat any suitable mammal, including primates, such as monkeys and humans, horses, cows, cats, dogs, rabbits, and rodents such as rats and mice. In one embodiment, the mammal to be treated is human.

In another aspect, the invention also includes screening methods for identifying a tumor mitochondrial antigen molecule. In one example, the invention includes a method for identifying a tumor mitochondrial antigen, the method comprising: screening a library of mitochondrial mutant molecules; and identifying a molecule that effectively stimulates an anti-tumor immune response.

All patents and literature references cited in the present specification are hereby incorporated by reference in their entirety.

The following examples are presented in order to more fully illustrate the preferred embodiments of the invention. They should in no way be construed, however, as limiting the broad scope of the invention.

EXAMPLES

Example 1: Tumor Mitochondria Protein Pulsed Dendritic Cell Immunization Confers Tumor Protection Our results indicate that dendritic cells pulsed with "tumor mitochondrial lysates" can elicit anti-tumor responses that significantly impact tumor development in model systems.

Figure 1C:
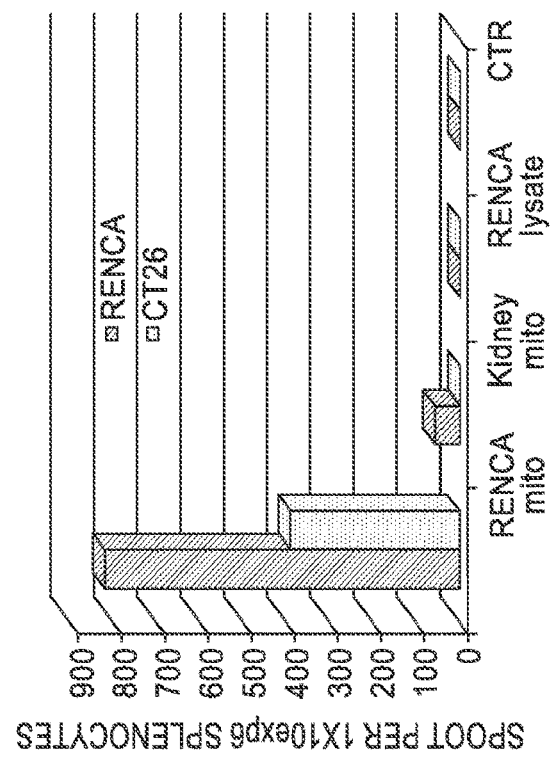
Figure 1B:
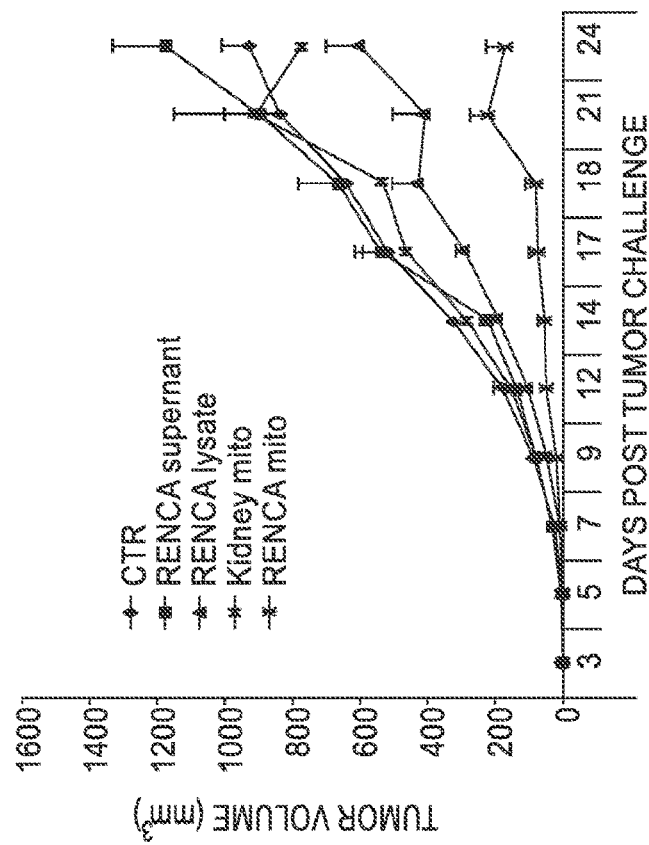
Figure 2A:
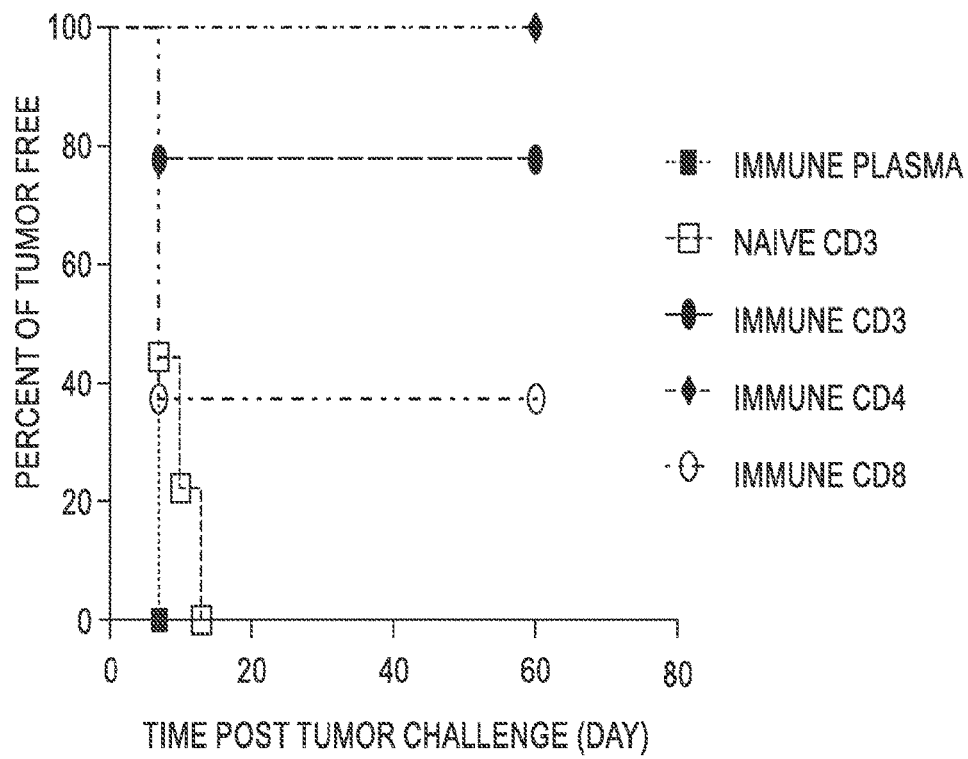
FIG. 2 shows that tumor mitochondria protein pulsed dendritic cell immunization induces T cell dependent protection and memory. A. Percent of tumor free in immune plasma, naïve CD3, immune CD3, immune CD4, and immune CD8. B. Adaptive schedule. C. Percent of tumor free in DC/PBS, DC/Liver mito, and DC/Renca mito. D. Memory schedule.
Figure 2B:
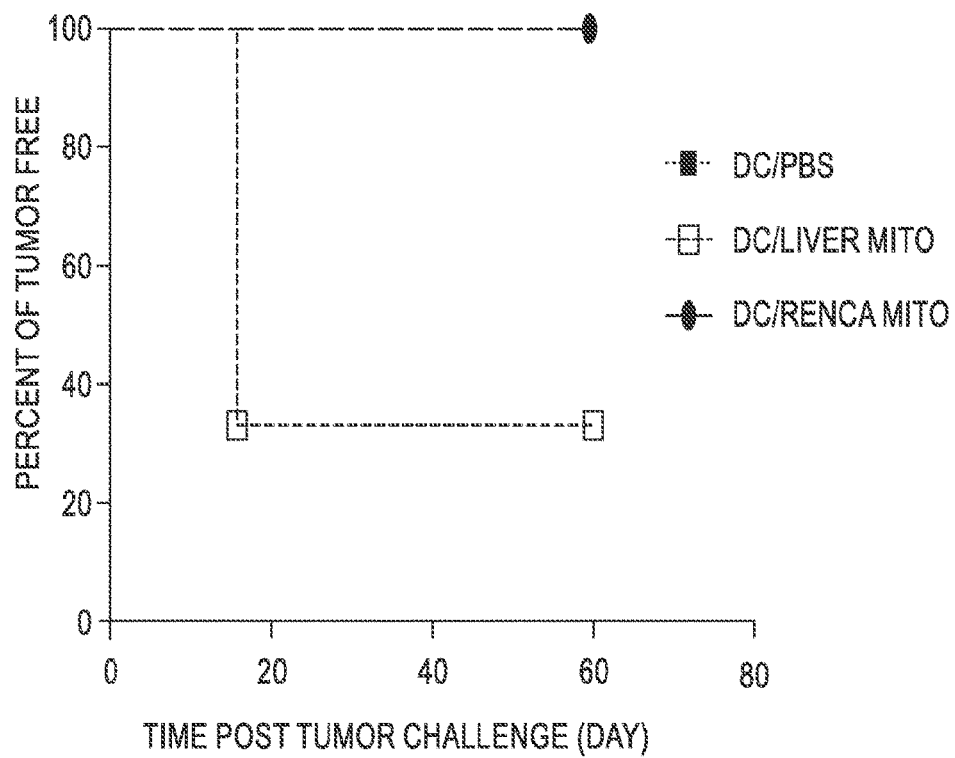
Figure 2C:
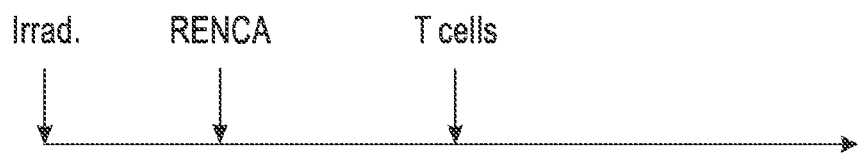
Figure 2D:
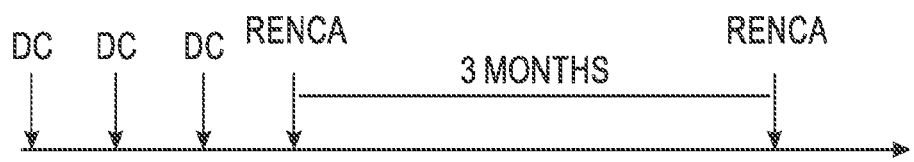
Figure 3:
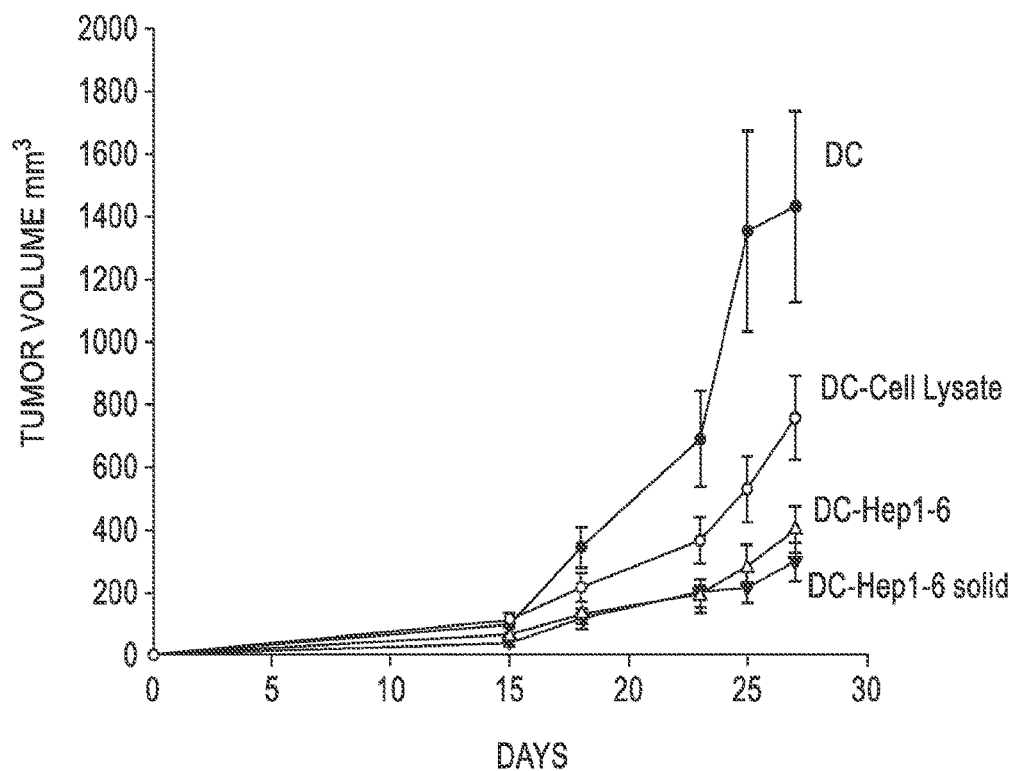
FIG. 3 shows that tumor mitochondria protein pulsed dendritic cell immunization confers tumor protection for a hepatocarcinoma mouse model.
Figure 3:
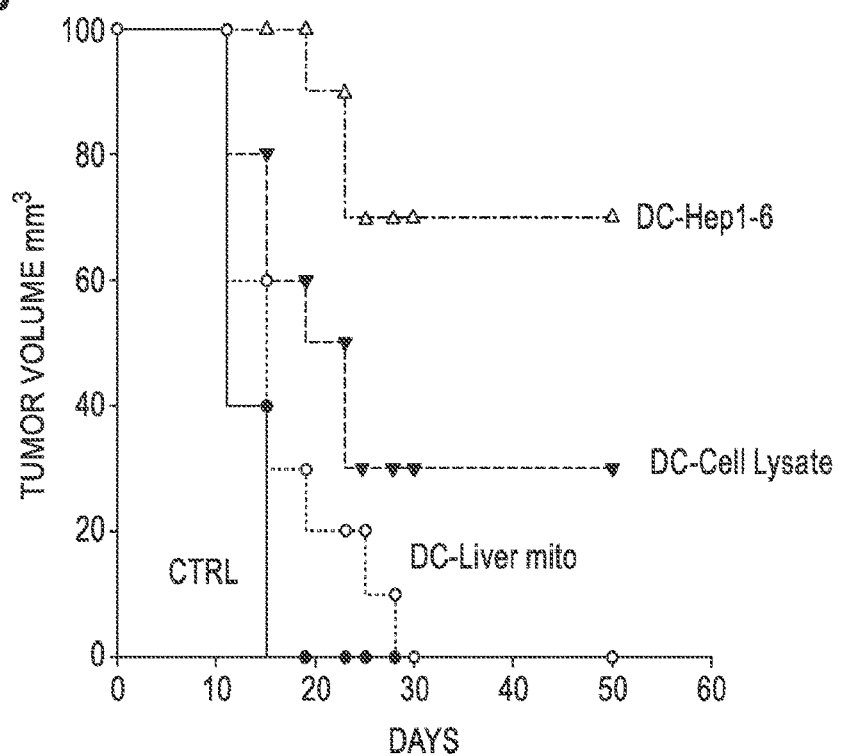
Figure 4:
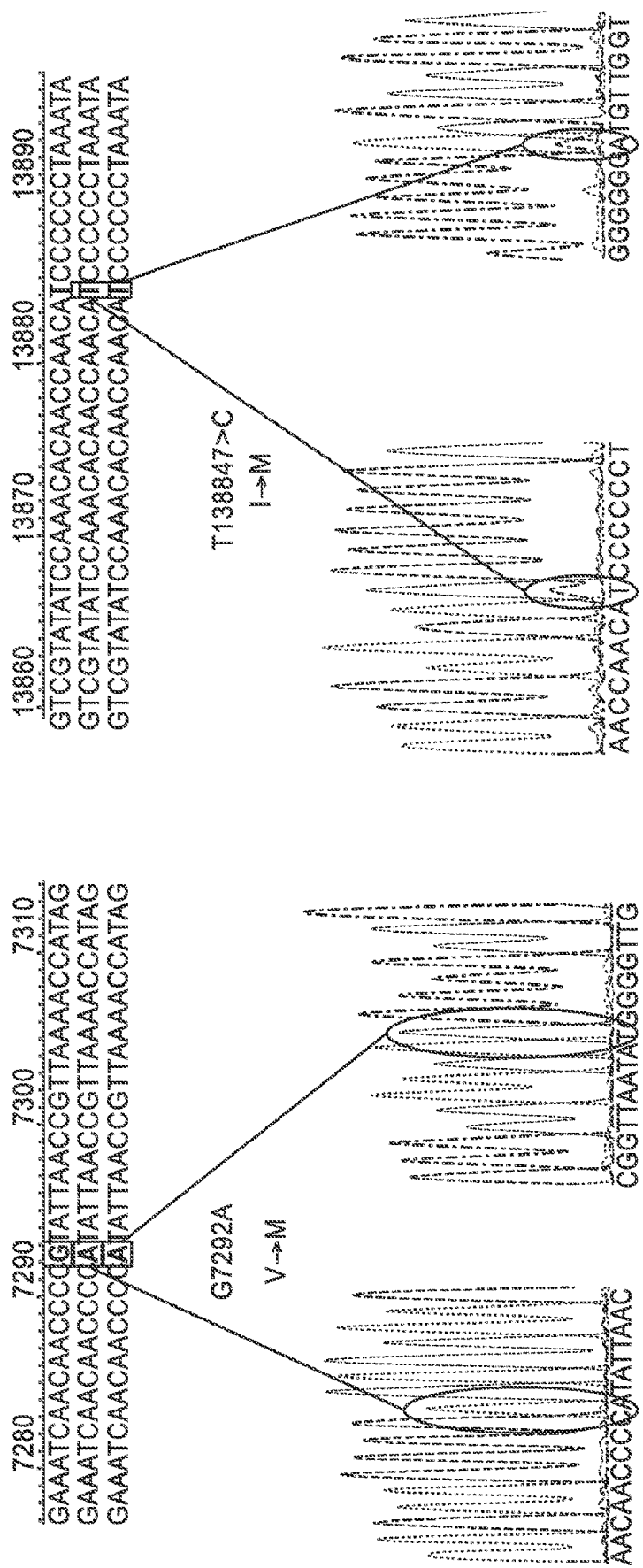
FIG. 4. Hep1-6 harbors a homoplasmic mutation in Cyclooxygenase-2 (COX-2) and an heteroplasmic mutation in NADH dehydrogenase 6 (ND6).

We demonstrated in animal models (i.e., mice models) of renal or hepato-carcinoma that both solid tumor and tumor cell-derived mitochondrial protein lysates can pulse syngeneic bone marrow derived DC (BM-DC); following maturation of these pulsed DCs with LPS and IFNg they act as potent antitumor vaccines. Administration of these tumor mitochondria-pulsed BM-DC resulted in rejection of 70 percent of tumors when the vaccine was given prophylactically and 50 percent of tumors when given therapeutically; in both cases, significant delay in tumor growth was observed in the remaining animals (FIG. 1B). To assess the adaptive immune response, 100,000 purified CD3+ T cells isolated from splenocytes of vaccinated animals were exposed to tumor cells at a ratio of 10:1 and an interferon gamma ELISPOT assay performed on the cell culture supernatant. T cells from tumor mitochondria-treated animals responded vigorously to tumor cells, while controls did not (FIG. 1C).

Next, we verified the T cell or antibody dependence of the tumor rejection by passive transfer of T cells or serum from animals that reject the tumor during the first challenge in new tumor bearing animals Serum or splenocytes from "first challenge surviving animals" were obtained, T cells purified and dived in CD3+CD4+, CD3+CD8+ and CD3+ and i.v. administered in tumor bearing animals. Next we asked if our vaccine would be capable to induce immunological memory, some of the animals that reject the tumor in first instance were re-challenged 3 months later.

Finally, we sequenced the 13 CDS present in the mitochondrial DNA and identified 2 non conservative point mutations. The first one is located in the COX-1 CDS and is COX-1 G6234A. This mutation replaces the corresponding alanine (Ala) residue with threonine (Thr) residue. The second one is located in the CDS of the ND5, which is C13330A. This mutation replaces the corresponding proline (Pro) residue with threonine (Thr) residue. These mutants, in either nucleic acid or protein levels, can be used as antigen source.

Hep1-6 is a model of hepatocarcinoma mouse model in a C57L background. As done for the Renal Cancer model RECA, mitochondria purified from in vitro culture, Hep1-6 cells were extracted and used to pulse immature dendritic cells. Pulsed dendritic cells were than matured with a cocktail of IFNg/LPS overnight and used to immunize mice 3 days prior to challenge.

Next mitochondrial DNA from Hep1-6 or healthy liver form C57L mice were amplified, sequenced and aligned (FIG. 5). The alignment identified two TAMAs, one localized within the Cyclooxygenase-2 (COX-2) and the second within the NADH dehydrogenase 6 (ND6) coding sequences. The first one located in the COX-2 CDS is G7292A; this mutation replaces the corresponding valine (Val) residue with a methionine (Met) residue. The second one located in the CDS of the ND6 CDS is T13884T>C; this mutation replaces the corresponding isoleucine (He) residue with a methionine (Met) residue.

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

What is claimed is:

1. A tumor-specific immunogenic composition comprising: an antigen-presenting cell pulsed with a tumor mitochondrial protein lysate from a renal cancer or a liver cancer, and wherein said antigen-presenting cell is a dendritic cell.

2. The composition of claim 1, wherein the composition comprises a buffered medium.

3. The immunogenic composition of claim 1, wherein the dendritic cell is an autologous dendritic cell from a subject having the renal cancer or the liver cancer.

4. The immunogenic composition of claim 1, wherein the tumor mitochondrial protein lysate is from a renal cancer.

5. The immunogenic composition of claim 1, wherein the tumor mitochondrial protein lysate is from a liver cancer.

6. A method for stimulating an anti-tumor immune response in a subject, the method comprising: administering a therapeutically effective amount of the immunogenic composition of claim 1 to said subject.

7. The method of claim 6, wherein said antigen-presenting cell is a dendritic cell.

8. The method of claim 6, wherein said tumor antigen is associated with a renal cancer or a liver cancer.

9. The method of claim 6, wherein the composition comprises a buffered medium.

10. The method of claim 6, wherein said subject is a human subject.

11. A method for treating a renal cancer or a liver cancer by immunotherapy in a subject, the method comprising: administering a therapeutically effective amount of the immunogenic composition of claim 1 to said subject.

12. The method of claim 11, wherein said antigen-presenting cell is a dendritic cell.

13. The method of claim 11, wherein the composition comprises a buffered medium.

14. The method of claim 11, wherein said subject is a human subject.

* * * * *

SEQUENCE LISTING

```
<160> NUMBER OF SEQ ID NOS: 6

<210> SEQ ID NO 1
<211> LENGTH: 37
<212> TYPE: DNA
<213> ORGANISM: Mus musculus

<400> SEQUENCE: 1
gaaatcaaca accccgtatt aaccgttaaa accatag                             37

<210> SEQ ID NO 2
<211> LENGTH: 37
<212> TYPE: DNA
<213> ORGANISM: Mus musculus

<400> SEQUENCE: 2
gaaatcaaca accccatatt aaccgttaaa accatag                             37

<210> SEQ ID NO 3
<211> LENGTH: 37
<212> TYPE: DNA
<213> ORGANISM: Mus musculus

<400> SEQUENCE: 3
gaaatcaaca accccatatt aaccgttaaa accatag                             37
```

```
<210> SEQ ID NO 4
<211> LENGTH: 37
<212> TYPE: DNA
<213> ORGANISM: Mus musculus

<400> SEQUENCE: 4
tcgtatatcc aaacacaacc aacatccccc ctaaata                              37

<210> SEQ ID NO 5
<211> LENGTH: 37
<212> TYPE: DNA
<213> ORGANISM: Mus musculus

<400> SEQUENCE: 5
tcgtatatcc aaacacaacc aacatccccc ctaaata                              37

<210> SEQ ID NO 6
<211> LENGTH: 37
<212> TYPE: DNA
<213> ORGANISM: Mus musculus

<400> SEQUENCE: 6
tcgtatatcc aaacacaacc aacatccccc ctaaata                              37
```